United States Patent [19]
Van Gelder et al.

[11] Patent Number: 5,891,636
[45] Date of Patent: *Apr. 6, 1999

[54] PROCESSES FOR GENETIC MANIPULATIONS USING PROMOTERS

[75] Inventors: Russell N. Van Gelder, Menlo Park; Mark E. Von Zastrow, Los Altos; Jack D. Barchas, Stanford, all of Calif.; James H. Eberwine, Belcamp, Md.

[73] Assignee: Board of Trustees of Leland Stanford University, Palo Alto, Calif.

[ * ] Notice: The term of this patent shall not extend beyond the expiration date of Pat. Nos. 5,545,522 and 5,716,785.

[21] Appl. No.: 922,965

[22] Filed: Sep. 3, 1997

Related U.S. Application Data

[63] Continuation of Ser. No. 636,748, Apr. 19, 1996, Pat. No. 5,716,785, which is a continuation of Ser. No. 957,647, Oct. 5, 1992, Pat. No. 5,545,522, which is a continuation of Ser. No. 411,370, Sep. 23, 1989, abandoned.

[51] Int. Cl.$^6$ .............................. C12Q 1/68; C12P 19/34; C03H 21/04
[52] U.S. Cl. ..................... 435/6; 435/91.21; 435/91.51; 536/23.1; 536/24.1; 536/24.3; 536/24.33; 536/24.5
[58] Field of Search ..................... 435/6, 91.21, 91.51; 536/23.1, 24.1, 24.3, 24.33, 24.5

[56] References Cited

U.S. PATENT DOCUMENTS

| | | | |
|---|---|---|---|
| 4,683,195 | 7/1987 | Mullis et al. ................................ | 435/6 |
| 4,683,202 | 7/1987 | Mullis ..................................... | 435/91.2 |
| 4,981,783 | 1/1991 | Augenlicht ................................ | 435/6 |
| 5,057,410 | 10/1991 | Kawasaki et al. .......................... | 435/6 |
| 5,085,983 | 2/1992 | Scanlon ..................................... | 435/6 |
| 5,130,238 | 7/1992 | Malek et al. .......................... | 435/91.21 |
| 5,281,519 | 1/1994 | Schechter et al. ........................... | 435/6 |
| 5,514,545 | 5/1996 | Eberwine ..................................... | 435/6 |
| 5,545,522 | 8/1996 | Van Gelder et al. ....................... | 435/6 |
| 5,569,584 | 10/1996 | Augenlicht ................................. | 435/6 |
| 5,716,785 | 2/1998 | Van Gelder et al. ....................... | 435/6 |

FOREIGN PATENT DOCUMENTS

| | | |
|---|---|---|
| 0373960 | 6/1990 | European Pat. Off. . |
| WO 88/10315 | 12/1988 | WIPO . |
| WO 89/01050 | 2/1989 | WIPO . |
| WO 89/06700 | 7/1989 | WIPO . |

OTHER PUBLICATIONS

Behnam et al., "Multiplicity of glutamate receptor subunits in single striatal neurons: An RNA amplification study," *Molecular Pharmacology*, 49:852–859, 1996.

Belldegrun et al., "Lymphokine mRNA profile and functional analysis of a human CD4$^+$ clone with unique antitumor specificty isolated from renal cell carcinoma ascitic fluid," *Cancer Immunol. Immunother.*, 31:1–10, 1990.

Belyavsky et al., "PCR–based cDNA library contruction: General cDNA libraries at the level of a few cells," *Nucleic Acids Research*, 1798):2119–2932, 1989.

Berger et al., "Reverse transcriptase and its associated ribonuclease H: Interplay of two enzyme activities controls the yield of single–stranded complementary deoxyribonucleic acid," *Biochemistry*, 22:2365–2372, 1983.

Chan, "Nucleotide sequence of the *Staphylococcus aureus* PC1 β–lactamase gene," *Nucleic Acids Rs.*, 14914):5940, 1986.

Chang et al., "The nucleotide sequence of the untransulated 5' regions of human α–and β–globin MRNAs," *Proc. Natl. Acad. Sci. USA*, 74(11):5145–5149, 1977.

Chicurel et al., "mRNA at the synapse: Analysis of a synaptosomal preparation enriched in hippocampal dendritic spines," *The Journal of neuroscience*, 1399):4054–4063, 1993.

Craig et al., "Development expression of morphoregulatory genes in the mouse embryo: an analytical approach using a novel technology," *Biochemical and Molecular Medicine*, 60:81–91, 1997.

Craig et al., "The distribution of glutamate receptors in cultured rat hippocampal neurons: Postsynaptic clustering fo AMPA–selective subunits," *Neuron*, 10:1055–1068, 1993.

Davis et al., "Use of telost saccule to identify genes involved in inner ear function," *DNA and Cell Biology*, 14(10):833–839, 1995.

Eberwine et al., *Neuroscience Short Course 1 (Society for Neuroscience)*, pp. 69–81, 1988.(copy of reference unavailable; refer to Information Disclosure Statement filed Nov. 30, 1989 In SN 07/411,370.

Eberwine et al., "Analysis of gene expression in single live neurons," *Proc. Natl. Acad. Sci. USA*, 89:3010–3014, 1992.

Eberwine et al., "mRNA structure, in situ, as assessed by microscopic techniques," *Microscopy Research and Technique*, 25:19–28, 1993.

Efstratiadis et al., "Enzymatic in vitro synthesis of globin genes," *Cell*, 7:279–288, 1976.

Feinberg et al., "A Technique for Radiolabeling DNA Restriction Endonuclease Fragments to High Specific Activity," *Advanced Biochemistry*, 132:6–13, 1983.

Finnell et al., "Lack of concordance between heat shock proteins and the development of tolerance to teratogen–induced neural tube defects," *Developmental Genetics*, 14:137–147, 1993.

Firestein, et al., "Quantitative analysis of cytokine gene expression in rheumatoid arthritis," *J. Immunology*, 144(9):3347–3353, 1990.

(List continued on next page.)

*Primary Examiner*—James Ketter
*Assistant Examiner*—William Sandals
*Attorney, Agent, or Firm*—Arnold, White & Durkee

[57] ABSTRACT

This invention relates to the use of promoters for ribonucleic acid amplification and other genetic manipulations. Processes are provided wherein complementary deoxyribonucleic acid (cDNA) is synthesized from a ribonucleic acid (RNA) sequence using a complementary primer linked to an RNA polymerase promoter region complement and then anti-sense RNA (aRNA) is transcribed from the cDNA by introducing an RNA polymerase capable of binding to the promoter region. Additional processes using the resulting aRNA are also described.

54 Claims, 1 Drawing Sheet

OTHER PUBLICATIONS

Frohman et al., "Rapid production of full–length cDNAs from rare transcripts: Amplification using a single gene–specific oligonucleotide primer," *Proc. Natl. Acad. Sci. USA*, 85:8998–9002, 1988.

Gould et al., "Use of the DNA polymerase chain rection for homology probing: Isolation of partial cDNA or genomic clones encoding the iron–sulfur protein of succinate dehydrogenase from several species," *Proc. Natl. Acad. Sci. USA*, 86:1934–1938, 1989.

Gubler and Hoffman, "A simple and very efficient method for generating cDNA libraries," *Gene*, 25:263–269, 1983.

Hames et al., *Nucleic Acids Hybridization*, IRL Press, Washington, D.C., pp. 179–202, 1985. (copy of reference unavailable; cited bt Examiner Chambers in an Office Action dated Jun. 24, 1993 in SN 07/957,647).

Harlan, "Regulation of neuropeptide gene expression by steroid hormones," *Molecular Neurobiology*, 2:183–200, 1988.

Huang and Hershey, "Translational initiation factor expression and ribosomal protein gene expression are repressed coordinately but by different mechanisms in murine lymphosarcoma cells treated with glucocorticoids," *Mol. and Cell. Biology*, 9(9):3679–3684, 1989.

Jaakkola et al., "Type 1 neurofibromatosis: selective expression of extracellular matrix genes by Schwann cells, perineurial cells, and fibroblasts in mixed cultures," *J. Clin. Invest.*, 84:253–261, 1989.

James and Pearce, "The influence of adjuvant on induction of protective immunity by a non–living against schistosomiasis," *J. Immunol.*, 140(8):2753–2759, 1988.

Liang and Pardee, "Differential display of eukaryotic messenger RNA by menas of the polymerase chain reaction," *Science*, 257:967–971, 1992.

Lockhart et al., "Expression monitoring by hybridization to high–density oligonucleotide arrays," *Nature Biotechnology*, 14:1675–1680, 1996.

Mackler and Eberwine, "Cellular adaption to opiates alters ion–channel mRNA levels," *Proc. Natl. Acad. Sci. USA*, 91:385–389, 1994.

Mackler and Eberwine, "Diversity of glutamate receptor subunit mRNA expression within live hippocampal CAI neurons," *Mol. Pharm.*, 44:308–315, 1992.

Mackler and Eberwine, "The molecular biology of addicitive drugs," *Mole. Neuro.*, 5:45–58, 1991.

Mackler et al., "Stimulus–induced coordinate changes in mRNA abundance in single postsynaptic hippocampal CAI neurons," *Neuron*, 9:539–548, 1992.

Mattson and Kater, "Development and selective neurodegeneration in cell cultures from different hippocampal regions," *Brain Research*, 490:110–125, 1989.

McLaren and Goodard, The nucleotide sequence of a human $tRNA^{Leu}$ gene, *Nucleic Acids Res.*, 14(14):5938, 1996.

Melton et al., "Efficient in vitro synthesis of biologically active RNA and RNA hybridization probes from plasmids containing a bacteriophage SP6 promoter," *Nucl. Acids Res.*, 12(18):7035–7055, 1984.

Meyers et al., "Human leukocyte antigen II, interleukin–6, and interleukin–6 receptor expression determined by the polymerase chain reaction," *Cancer*, 67(8):2087–2095, 1991.

Milner and Sutcliffe, "Gene expression in rat brain," *Nucl. Acids. Res.*, 11(16):5497–5521, 1983.

Nair et al., "Corticosteroid regulation of ion channel conductances and mRNA levels in individual hippocampal CA 1 neurons," *J. Neuroscience*, 18(7):2685–2696, 1988.

Naylor and van de Sande, "Improved sequence resolution of highly repetitive DNA fragments," *Nucleic Acids Res.*, 14(14):5939, 1986.

FIG. 1

PROCESSES FOR GENETIC MANIPULATIONS USING PROMOTERS

This is a Continuation of application No.—U.S. Ser. No. 08/636,748, filed Apr. 19, 1996 now U.S. Pat. No. 5,716,785 which is a continuation of U.S. Ser. No. 07/957,647, filed Oct. 5, 1992, now U.S. Pat. No. 5,554,552 which is a continuation of U.S. Ser. No. 07/411,370 filed Sep. 23, 1989 now abandoned.

FIELD OF THE INVENTION

The present invention relates generally to the field of recombinant DNA technology and, more particularly, to improved methods for producing amplified heterogeneous populations of RNA from limited quantities of cDNA or other nucleic acids.

BACKGROUND OF THE INVENTION

Selective amplification of cDNA's represents a major research goal of molecular biologists, with particular importance in diagnostic and forensic applications, as well as for general manipulations of genetic materials.

In many important areas of research, such as in studying gene regulation in complex biological systems (e.g., the brain) having multiple phenotypes, obtaining sufficient mRNA for the isolation, cloning, and characterization of specific regulated transcripts is problematic. Research has been hindered by, e.g., the high complexity of the mRNA, the relatively low abundance of many important expressed messages, and the spatially limited expression of these messages. In particular, the identification and cloning of novel regulated messages from discrete cell populations has proven to be a formidable task.

The polymerase chain reaction (PCR) is an extremely powerful technique for amplifying specific nucleic acid sequences, including mRNA in certain circumstances. As described in U.S. Pat. Nos. 4,683,202 and U.S. Pat. No. 4,683,195 (both of which are incorporated herein by reference), PCR typically comprises treating separate complementary strands of a target nucleic acid with two oligonucleotide primers to form complementary primer extension products on both strands that act as templates for synthesizing copies of the desired nucleic acid sequences. By repeating the separation and synthesis steps in an automated system, essentially exponential duplication of the target sequences can be achieved.

PCR, however, has several well-known limitations. For example, PCR typically requires that 5' terminus and 3' terminus sequence information be known for the synthesis of the primers. Recently, homopolymeric tailing of the 3' terminus (see Frohman, et al., Proc. Natl. Acad. Sci. U.S.A. 85: 8998–9002 (1988) and Eberwine et al., Neuroscience Short Course I (Society for Neuroscience) 69–81 (1988)) and the synthesis of highly degenerate nucleotide primers (Gould et al., Proc. Natl. Acad. Sci. U.S.A. 86: 1934–1938 (1989)) have been implemented to improve the range of cDNAs that can be cloned with PCR. An additional problem is the low fidelity of the most widely used enzyme in PCR, *Thermus aquaticus* (Taq) polymerase. This characteristic of Taq results in misincorporations that are propagated through the subsequent cycles of PCR amplification—ultimately producing faulty cDNA libraries. Also, sequences longer than 3 kilobases create difficulties in Taq transcription, which can skew cDNAs to smaller sizes during amplification. Of course, unless modified, PCR provides amplification by DNA replication and not by transcription.

In this regard, Sarkar et al., Science 244: 331–34 (1989), recently described a method, called RAWTS (RNA amplification with transcript sequencing), for detecting extremely low abundance messages in heterologous cell types. This method is a modification of GAWTS (genomic amplification with transcript sequencing; see, Stofler, et al., Science 239: 491 (1988)), which incorporates a phage promoter into at least one of the two primers used in PCR. In RAWTS, mRNA is amplified by PCR. A phage promoter incorporated into the PCR oligonucleotide primer allows abundant transcription, from which RNA can be sequenced directly.

Four steps are used in RAWTS: (1) first strand cDNA synthesis from total RNA or mRNA using oligo(dT) or an mRNA-specific oligo primer, dNTPs, and reverse transcriptase; (2) PCR, wherein one or both primers contain a T7 phage promoter attached to a sequence complementary to the region to be amplified; (3) transcription of the cDNA strand with T7 RNA polymerase; and (4) reverse transcriptase-mediated dideoxy sequencing of the resultant mRNA transcript.

In spite of such recent advances, including PCR and its various modifications noted above, there exists a need for improved methods of identifying and cloning mRNAs and of accurate in vitro amplification of selected cDNA's. The methods should produce about 100-fold or more amplification of heterogeneous populations of RNA from limited quantities of cDNA. Preferably, the overall methodologies will be capable of replicating a broad range of messages without prior cloning into vectors and without knowledge of sequence in some instances. The present invention fulfills these and other needs.

SUMMARY OF THE INVENTION

The present invention provides novel processes for amplifying at least one sequence in a collection of nucleic acids sequences, the processes comprising (i) synthesizing a nucleic acid by hybridizing a primer complex to the sequence and extending the primer to form a first strand complementary to the sequence and a second strand complementary to the first strand, wherein the complex comprises a primer complementary to the sequence and a promoter region in anti-sense orientation with respect to the sequence; and (2) transcribing copies of anti-sense RNA off of the second strand. The promoter region, which may be single or double stranded, is capable of inducing transcription from an operably linked DNA sequence in the presence of ribonucleotides and a RNA polymerase under suitable conditions. Suitable promoter regions are prokaryotes, such as from T3 or T7 bacteriophage. The primer is preferably a single stranded nucleotide, of sufficient length to act as a template for synthesis of extension products under suitable conditions and maybe poly(T) or a collection of degenerate sequences.

In another aspect, the invention is directed to a processes for detecting expression of a gene in a preselected cell population comprising steps of:
  (a) synthesizing double-stranded cDNA by treating mRNAs from the cell populations with a primer complex comprising an oligonucleotide complementary to one or more of the RNA sequences, the primer linked to a promoter region in an orientation capable of directing transcription of anti-sense RNA;
  (b) transcribing the cDNA into anti-sense RNA by introducing an RNA polymerase capable of operably binding to the promoter region; and
  (c) determining the presence or absence of transcribed anti-sense RNA complementary to mRNA corresponding to the gene.

The cell population may be, e.g., from a human tissue, such as brain nuclei. The cell population may be single cell, or up to 100 to 1,000,000 cells or more as desired.

In another embodiment, the present invention comprises a process for producing a subtractive hybridization probe comprising:

(a) synthesizing a first double-stranded cDNA collection by treating a first mRNA population with a primer complex, wherein the primer is complementary to the RNA sequence and is operably linked to a first promoter region for transcription of the cDNA strand complementary to the primer;

(b) transcribing the first cDNA into anti-sense RNA by introducing a first RNA polymerase capable of binding to the first promoter region;

(c) hybridizing the anti-sense RNA to a second mRNA population, whereby an unhybridized subpopulation of the second RNA population is found;

(d) generating a second double-stranded cDNA collection from the unhybridized subpopulation using a second primer complex comprising a second promoter region in an orientation for transcribing anti-sense RNA complementary to the unhybridized subpopulation; and (e) transcribing the second cDNA into a ribonucleotide probe by introducing a second RNA polymerase capable of binding to the second promoter region.

Additionally, the present invention comprises methods for making cDNA libraries from a collection of mRNA molecules comprising the steps of:

(a) hybridizing one or more primer complexes to a plurality of the mRNA's, wherein each complex comprises an oligonucleotide primer linked to a promoter sequence capable of directing transcription of a DNA sequence complementary to the primer;

(b) producing a collection of double-stranded cDNAs by extending the primers of a plurality of any hybridization duplexes formed between the mRNA's and the complexes wherein each cDNA comprises a first strand complementary to one mRNA molecule and a second strand operably linked to the promoter sequence;

(c) transcribing multiple copies of anti-sense RNA off of the second strand; and (d) preparing a cDNA library from the anti-sense RNA copies.

Importantly, the present invention can be readily provided in kit form for a variety of uses. In addition to instructions, a kit will typically comprise containers of reverse transcriptase, RNA polymerase, and nucleotides which may be labelled, such as with radioactive labels (e.g., $^{14}C$, $^{3}H$, $^{32}P$ and the like).

BRIEF DESCRIPTION OF THE FIGURE

FIG. 1. Paradigm for production of amplified, anti-sense RNA (aRNA). Whole RNA is reverse transcribed using a synthetic primer containing the T7 RNA Polymerase binding site (5' AAA CGA CGG CCA GTG AAT TGT AAT ACG ACT CAC TAT AGG GCG (T)$_{15}$ 3'). Second strand cDNA synthesis (producing double-stranded (ds) cDNA) is performed using RNase H and *E. coli* DNA polymerase I (Gubler and Hoffman, Gene 25: 263–269 (1983)). Following blunt-ending of cDNA with T4 DNA polymerase (at which point a functional T7 RNA polymerase promoter is created), the cDNA is purified and transcribed with T7 RNA polymerase, yielding amplified, anti-sense RNA.

DETAILED DESCRIPTION OF THE SPECIFIC EMBODIMENTS

Figure 1:
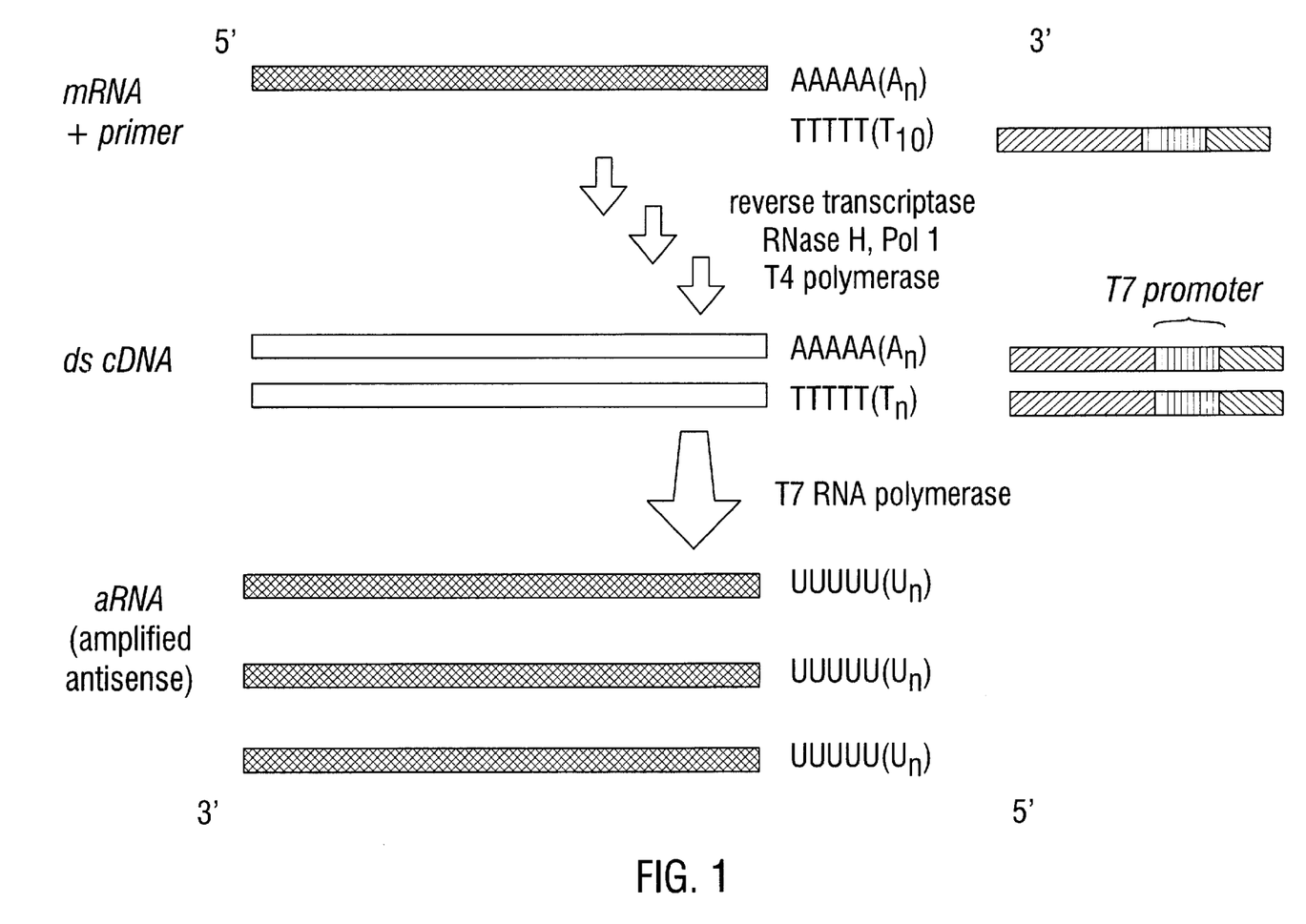

In accordance with the present invention, novel methods and compositions are provided for the amplification of broad classes of cDNAs. In typical embodiments, as shown in FIG. 1, these methods involve the incorporation of an RNA polymerase promoter into selected cDNA molecule by priming cDNA synthesis with a primer complex comprising a synthetic oligonucleotide containing the promoter. Following synthesis of double-stranded cDNA, a polymerase generally specific for the promoter is added, and anti-sense RNA is transcribed from the cDNA template. The processive synthesis of multiple RNA molecules from a single cDNA template results in amplified, anti-sense RNA (aRNA) that serves, inter alia, as starting material for cloning procedures using random primers. The amplification, which will typically be at least about 20–40, typically to 50 to 100 or 250-fold, but may be 500 to 1000-fold or more, can be achieved from nanogram quantities or less of cDNA, and is economical, simple to perform under standard molecular biology laboratory conditions (see, Maniatis et al., (1982), *Molecular Cloning: A Laboratory Manual*, Cold Spring Harbor, which is incorporated herein by reference). It is also easily adaptable into kit form.

The techniques of the present invention also provide a number of additional genetic manipulation technologies. The aRNA represents a useful intermediate for construction of complex cDNA libraries from extremely limited amounts of tissue, such as individual brain nuclei, tissue sections, and even single cells. Also, with appropriate amplification primers, aRNA synthesis can be used for the production of specific ribonucleotide probes without prior cDNA cloning into riboprobe vectors. Further, aRNA provides a source of large amounts of single-stranded, anti-sense material for use as driver in subtractive hybridization. For example, two nucleic acid populations, one sense, and one anti-sense, can be allowed to mix together with one population present in molar excess (driver). Sequences present in both populations will form hybrids, whereas sequences present in only one population remain single-stranded (Duguid et al., Proc. Natl. Acad. Sci. U.S.A. 85: 5738–5742 (1988)).

In one general embodiment of the present invention, cDNA strands are synthesized from a collection of mRNA's using an oligonucleotide primer complex, i.e., a primer linked to a promoter region. If the target mRNA is the entire mRNA population, then the primer can be a polythymidylate region (e.g., about 5 to 20, preferably about 10 to 15 T residues), which will bind with the poly(A) tail present on the 3' terminus of each mRNA. Alternatively, if only a preselected mRNA is to be amplified, then the primer will be substantially complementary to a section of the chosen mRNA, typically at the 3' terminus. The promoter region is located upstream of the primer at its 5' terminus in an orientation permitting transcription with respect to the mRNA population utilized. This will usually, but not always, mean that the promoter DNA sequence operably linked to the primer is the complement to the functional promoter sequence. When the second cDNA strand is synthesized, the promoter sequence will be in correct orientation in that strand to initiate RNA synthesis using that second cDNA strand as a template. Preferably, the promoter region is derived from a prokaryote, and more preferably from the group consisting of SP6, T3 and T7 phages (Chamberlin and Ryan, in *The Enzymes*, ed. P. Boyer (Academic Press, New York) pp. 87–108 (1982), which is incorporated herein by reference). A preferred promoter region is the sequence from the T7 phage that corresponds to its RNA polymerase binding site (5' AAA CGA CGG CCA GTG AAT TGT AAT ACG ACT CAC TAT AGG GCG 3').

Once the oligonucleotide primer and linked promoter region hybridize to the mRNA, a first cDNA strand is synthesized. This first strand of cDNA is preferably produced through the process of reverse transcription, wherein DNA is made from RNA, utilizing reverse transcriptase following standard techniques. This enzyme, present in all retroviruses (e.g., avian myeloblastoma virus), adds deoxyribonucleotides to the 3' terminus of the primer (Varmus, Science 240: 1427–1435 (1988)).

The second strand cDNA, creating double-stranded (ds) cDNA, can be synthesized by a variety of means, but preferably with the addition of RNase H and *E. coli* DNA polymerase. RNase assists breaking the RNA/first strand cDNA hybrid, and DNA polymerase synthesizes a complementary DNA strand from the template DNA strand. The second strand is generated as deoxynucleotides are added to the 3' terminus of the growing strand. As the growing strand reaches the 51' terminus of the first strand DNA, the complementary promoter region of the first strand will be copied into the double stranded promoter sequence in the desired orientation.

Thereafter, cDNA is transcribed into anti-sense RNA (aRNA) by introducing an RNA polymerase capable of binding to the promoter region. The second strand of cDNA is transcribed into aRNA, which is the complement of the initial mRNA population. Amplification occurs because the polymerase repeatedly recycles on the template (i.e., reinitiates transcription from the promoter region). Importantly, this particular technique thus enables replicating a broad range of cDNA's without prior cloning into vectors. Recycling of the polymerase on the same template avoids propagation of errors.

The RNA polymerase used for the transcription must be capable of operably binding to the particular promoter region employed in the primer complex. A preferred RNA polymerase is that found in bacteriophages, in particular T3 and T7 phages. Substantially any polymerase/promoter combination can be used, however, provided the polymerase has specificity for that promoter in vitro sufficient to initiate transcription.

The most preferred polymerase is T7 RNA polymerase. The extremely high degree of specificity shown by T7 RNA polymerase for its promoter site (Chamberlin et al., in *The Enzymes*, ed. P. Boyer (Academic Press, New York) pp. 87–108 (1982)) has previously made this enzyme a useful reagent in a variety of recombinant DNA techniques, including in vitro RNA synthesis from plasmids containing the promoter site for use as probes (Melton et al., Nucl. Acids Res., 12: 7035–7056 (1984)), for in vitro translation studies (Krieg et al., Nuc. Acids Res. 12: 7057–7070 (1984)), and for use in producing synthetic oligoribonucleotides (Milligan et al., Nuc. Acids Res. 15: 8783–8798 (1987)). The natural T7 promoters share a highly conserved sequence covering about bp −17 to about +6 relative to the start of the RNA chain (Dunn and Studier, J. Mol. Biol. 166: 477–535 (1983) and J. Mol. Biol. 175: 111–112 (1984), both of which are incorporated herein by reference). The lack of efficient termination signals for T7 polymerase also enable it to make transcripts from almost any DNA (see, Rosenberg et al., Gene 56: 125–135 (1987), which is incorporated herein by reference). The T7 polymerase is also available from a number of commercial sources, such as Promega Biotech, Madison, Wis., and in a concentrated form (1000 units/$\mu$l) from Epicenter Technologies, Madison, Wis. Other suitable polymerases include, by way of example and not limitation: T3 or SP6 (Promega) RNA polymerase and *E. coli* RNA polymerase, and will vary in accordance with the promoter region(s) utilized.

Depending on the ultimate use of the aRNA, included in the transcription reaction mixture will be the necessary nucleotide triphosphates, where one or more of the nucleotides may be labeled, particularly with a radioactive label, such as $^{32}$S, $^{32}$P, $^3$H, or the like. Alternatively, nucleotides may be obtained which are labeled with biotin, where these nucleotides will become incorporated in the aRNA (see, Sive and St. John, Nucl. Acids Res. 16: 10937 (1988) and Duguid et al., Proc. Natl. Acad. Sci. U.S.A. 85: 5738–5742 (1988) both of which are incorporated herein by reference). The biotin may then be used for binding to avidin, which is labeled with an appropriate label capable of providing for detection. A wide variety of labelling techniques are well known to those skilled in the art and may be used in accordance with standard procedures (see, U.S. Pat. No. 4,755,619, which is incorporated herein by reference).

In general, when characterizing the aRNA transcripts, various well known procedures may be employed. The transcripts may be removed from the reaction mixture and separated on an appropriate gel. The aRNA may be used as template for cDNA synthesis and subjected to PCR to further expand desired sequences. The aRNA may be used unmodified for further cloning, expression, use as probe or driver nucleic acid in subtractive hybridization, in Cot or Rot analysis, or the like.

Essentially any nucleic acid sequence, in purified or nonpurified form, can be utilized as the starting nucleic acid(s) for the methods of the present invention, provided it contains or is suspected to contain the specific nucleic acid sequence desired (i.e., complementary to the primer). It is only generally preferred that a sufficient number of bases at one end of the sequence be known in sufficient detail so that a primer template can be prepared which will hybridize to one of the strands of the desired sequence. A mixture of any of these nucleic acids may also be employed (including specific or degenerate sequences, see, e.g., PCR U.S. patents), or the nucleic acid produced from a previous amplification reaction using the same or different primers may be utilized. The specific nucleic acid sequence to be amplified may be only a fraction of a larger molecule or can be present initially as a discrete molecule, so that the specific sequence constitutes the entire nucleic acid It is also not necessary that the sequence to be amplified be present initially in a pure form; it may be a minor fraction of a complex mixture, or a portion of a nucleic acid sequence, the existence of which is due to a particular microorganism's presence. The starting nucleic acid sequence may contain more than one desired specific nucleic acid sequence, each of which may be the same or different from each other. Therefore, the amplification process is useful not only for producing large amounts of one specific nucleic acid sequence, but also for amplifying simultaneously more than one different specific nucleic acid sequence located on the same or different nucleic acid molecules.

The nucleic acid(s) may be obtained from any source, for example, from plasmids such as pBR322, from cloned DNA or RNA, or from natural DNA or RNA from any source, including bacteria, yeast, viruses, organelles, and higher organisms such as plants or animals. DNA or RNA may be extracted from blood, tissue material or cells by a variety of techniques such as those described by Maniatis et al., supra.

As used herein, the term "primer complex" refers to an oligonucleotide having two components: (1) a primer that may be synthetic or a purified restriction digest and (2) a specifically oriented RNA polymerase promoter region. The primer component will be capable of acting as a point of initiation of synthesis, typically DNA replication, when placed under conditions in which synthesis of a primer extension product that is complementary to a nucleic acid strand is induced, i.e., in the presence of appropriate nucleotides and a replicating agent (e.g., a DNA polymerase) under suitable conditions, which are well known in the art.

The primer is preferably a single stranded oligodeoxynucleotide. The primer must be sufficiently long to act as a template for the synthesis of extension products in the presence of the replicating agent. The exact lengths of the primers and the quantities used will depend on many factors, including temperature, degree of homology and other conditions. For example, when amplifying a specific sequence, the oligonucleotide primer typically contains between about 10 and 50 nucleotides, preferably 15–25 or more nucleotides, although it may contain fewer nucleotides, depending, e.g., on the promoter sequence. For other applications, the oligonucleotide primer is typically, but not necessarily, shorter, e.g., 7–15 nucleotides. Such short primer molecules generally require cooler temperatures to form sufficiently stable hybrid complexes with template.

The oligonucleotide primers may be prepared using any suitable method, such as, for example, the well known phosphotriester and phosphodiester methods, or automated embodiments thereof. In one such automated embodiment, diethylphosphoramidites are used as starting materials and may be synthesized as described by Beaucage et al., Tetrahedron Letters 22: 1859–1962 (1981). One method for synthesizing oligonucleotides on a modified solid support is described in U.S. Pat. No. 4,458,066. It is also possible to use a primer which has been isolated from a biological source (such as a restriction endonuclease digest).

The primers herein are selected to be "substantially" complementary to the different strands of each specific sequence to be amplified, i.e., the primers should be sufficiently complementary to hybridize with their respective strands. Therefore, the primer sequence need not reflect the exact sequence of the template, and can, in fact, be "degenerate." Non-complementary bases or longer sequences can be interspersed into the primer, provided that the primer sequence has sufficient complementarity with the sequence of the strand to be amplified to permit hybridization and extension.

Generally, it is not necessary to know the sequences of a target mRNA, as the primer may be a poly(T) of sufficient length to hybridize with substantially an entire population of messages (i.e., poly(T)$_n$, wherein n is typically from about 5 to 50 or more). Of course, when more sequence knowledge is available for a target RNA, the primer may be designed more specifically, which greatly increases the efficiency of the amplification. Moreover, the primer may actually comprise a collection of primer sequences, such as where more than one target sequence exists. Also, if there is ambiguity in the sequence information, a number of primers should be prepared. In particular, when any of several possible nucleic acid sequences encoding a protein could be correct based on a polypeptide sequence obtained from a fragment of the protein, a collection of primers containing sequences representing most or all of the possible codon variations (utilizing codon degeneracy) can be prepared.

Similarly, the promoter region will be capable of initiating transcription of an operably linked DNA sequence in the presence of ribonucleotides and an RNA polymerase under suitable conditions. The primer and promoter components will be linked in an orientation to permit transcription of a DNA strand that is complementary to the primer, i.e., the aRNA transcription will generally be in the same direction as the primer extension. A linker oligonucleotide between the components, if present, will typically comprise between about 5 and 20 bases, but may be smaller or larger as desired.

The second component of the primer complex, the promoter region, may be single stranded or double stranded. The region will usually comprise between about 15 and 250 nucleotides, preferably between about 25 and 60 nucleotides, from a naturally occurring RNA polymerase promoter or a consensus promoter region (Alberts et al., in *Molecular Biology of the Cell,* 2d Ed., Garland, N.Y. (1989), which is incorporated herein by reference). In general, prokaryotic promoters are preferred over eukaryotic promoters, and phage or virus promoters most preferred. As used herein, the term "operably linked" refers to a functional linkage between the affecting sequence (typically a promoter) and the controlled sequence.

Promoter sequences are regions where RNA polymerse bind tightly to the DNA and contain the start site and signal for RNA synthesis to begin. In *E. coli*, typically the RNA polymerase molecules covers about 60 nucleotides when it binds to the DNA. Native strong promoters typically contain two highly conserved DNA sequences, each about six nucleotides long, which are located upstream from the start site and separated from each other by about 17 nucleotides of unrecognized DNA. When promoters are compared, the regions of similarity are termed "consensus" sequences.

A wide variety of promoters and polymerases showing specificity for its cognate promoter are known. For example, the Bacillus subtilis phage SP01 synthesizes two or three new σ factors which, when combined with host RNA polymerase, recognize only SP01 promoters. Probably the best studied phage promoter/polymerase system is *E. coli* phage T7. T7 makes an entirely new polymerase that is highly specific for the 17 late T7 promoters. Rather than having two separate highly conserved regions like *515 E. coli* promoters, the late T7 promoters have a single highly conserved sequence from −17 to +6 relative to the RNA start site. The Salmonella phage SP6 is very similar to T7. The simplicity of the T3, T7, and SP6 systems have made them especially amendable to the expression of heterologous DNA in genetic engineering applications.

At least one example is known of an RNA polymerase which recognizes a single-stranded promoter. *E. coli* phage N4 makes an RNA polymerase which recognizes early N4 promoters on native single stranded N4 DNA. For a detailed description of promoters and RNA synthesis upon DNA templates, see Watson et al., *Molecular Biology of The Gene,* 4th Ed., Chapters 13–15, Benjamin/Cummings Publishing Co., Menlo Park, Calif., which is incorporated herein by reference.

As used herein the term "anti-sense orientation" means that the promoter will initiate transcription of the complementary sequence to the target sequence (for example., when mRNA is the target sequence of the primer, anti-sense RNA will be produced).

The high specificity of bacterial phage RNA polymerases for their cognate promoters, in particular, provides a novel subtractive hybridization paradigm, although other polymerase and promoters may be used. Because aRNA is anti-sense with respect to the input RNA, aRNA produced from RNA population #1 (using cDNA synthesized with, e.g., the T7 promoter-containing primer and T7 RNA polymerase) can be hybridized with RNA population #2. Unhybridized poly(A)+ RNA is then be transcribed into cDNA using reverse transcriptase and a primer containing a different RNA polymerase promotor (such as T3 or SP6).

Following second strand synthesis, these cDNAs are then be amplified with the addition of the appropriate RNA polymerase, yielding a high specific activity probe which is used to screen an appropriate cDNA or genomic library. Such a technique has an advantage over most other subtractive hybridization protocols in that physical separation of single and double stranded material is not required to generate the subtractive probe; additionally, the resultant aRNA can be radioactively labeled in excess of $1\times10^9$ cpm/µg (see, Melton, supra), permitting screening of a large number of clones with a limited amount of subtractive material.

Although the aRNA paradigms of the present invention will provide a useful adjunct to PCR in a wide variety of diagnostic or other studies, especially facilitated are studies of gene expression in essentially any mammalian cell or cell population. Although the cell may be from blood (e.g., white cells, such as T or B cells) a typical source of cell or tissue will be solid organs, such as brain, spleen, bone, heart, vascular, lung, kidney, liver, pituitary, endocrine glands, lymph node, dispersed primary cells, tumor cells, or the like. Thus, in the neural research area, identification of mRNAs which vary as a function of arousal state, behavior, drug treatment, and development, for example, has been hindered by both the difficulty in construction of cDNA libraries from small brain nuclei and in the relative spatial insensitivity of subtractive hybridization techniques. Use of the aRNA amplification method in construction of cDNA libraries from individual brain nuclei will provide for greater representation of low-abundance mRNAs from these tissues compared with their representation in whole brain cDNA libraries, and facilitate cloning of important low-abundance messages.

The RNA amplification technology can also be applied to improve methods of detecting and isolating nucleic acid sequences that vary in abundance among different populations, such as in comparing mRNA expression among different tissues or within the same tissue according to physiologic state. Methods for examining differential expression typically involve subtractive hybridization, wherein two nucleic acid populations, one sense and one anti-sense, are allowed to mix with one another. One population is present in molar excess ("driver") such that sequences represented in both populations form hybrids, whereas sequences present in only one population remain single-stranded. Thereafter, various well known techniques are used to separate the unhybridized molecules representing differentially expressed sequences.

Most methods of subtractive hybridization require that large amounts (generally tens of micrograms) of nucleic acid be available for use as "driver" in such experiments. This limits usefulness in examining differential expression of mRNAs present in a biological material that is available in small supply. This is overcome by cloning the nucleic acid populations of interest prior to subtraction, so that the cloning vector is used to amplify the amount of nucleic acid available for hybridization. However, because subtraction requires previous cloning, it is complicated, suffers from under- and over-representation of sequences depending on differences in growth rates in the mixed population, and may risk recombination among sequences during propagation of the mixed population. The aRNA technology of the present invention circumvents these problems by allowing production of large amounts of anti-sense RNA from limited amounts of nucleic acid, without the need for previous cloning. PCR produces both sense- and anti-sense strands, so is less favorable for this use.

An additional embodiment of the present invention is "differential amplification". This procedure allows amplification of only differentially expressed sequences by virtue of the specificity among prokaryotic RNA polymerase promoters.

Also, the novel aRNA technology is used to identify sequences of interest from small amounts of nucleic acid by detecting the amplified sequences in the aRNA product. The aRNA amplification is uniform among individual sequences, and thus, it is useful in estimating relative levels of representation of a given sequence relative to other sequences within a population. Such quantitative resolution finds use in molecular diagnostics (such as in diagnosing thalassemias characterized by abnormal levels of hemoglobin gene expression), where diagnosis can rest not on absolute presence or absence of a sequence, but on whether a given sequence is present at abnormally high or low levels relative to other sequences. By providing relatively linear amplification, the present invention offers advantages to PCR.

Anti-sense RNA has a wide variety of uses in both analytical research and therapeutics. Anti-sense RNA functions in several prokaryotic systems to regulate gene expression. Similarly, anti-sense RNA can regulate the expression of many eukaryotic genes. This permits blocking expression of undesirable genes. Therapeutic use of anti-sense RNA therefore involves in vitro synthesis of anti-sense RNA with subsequent introduction into the subject (see, generally, Melton, *Antisense RNA and DNA*, Cold Spring Harbor (1988), which is incorporated herein by reference).

Another application of the inventive aRNA technology is in detection of variant regions flanking a common sequence, such as for molecular diagnostics. By designing an amplification primer that recognizes a commonly shared sequence, aRNA is produced that contains not only the common region recognized by the primer, but also 5'-flanking sequence useful in detecting sequence variants. An advantage over PCR is that only one region of shared sequence need be known; PCR generally requires that shared sequences be known both 5'- and 3'- to the region of interest, and that these flanking regions be sufficiently close to allow efficient amplification. Thus, for example, aRNA can be produced from limited amounts of clinical material to allow pathogen-specific sequences (such as those distinguishing viral types) to be identified, genetic polymorphisms to be detected, or alternate splicing variants to be characterized, all in accordance with standard techniques.

The materials for use in the methods of the present invention are ideally suited for preparation of kits produced in accordance with well known procedures. Such a kit may comprise containers, each with one or more of the various reagents (typically in concentrated form) utilized in the methods, including, for example, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more primer complexes of the present invention (e.g., appropriate length poly(T) or random primers linked to a promoter reactive with the RNA polymerase). A set of instructions will also typically be included.

The following experimental examples are offered by way of illustration and not by way of limitation.

EXPERIMENTAL

Materials

Avian myeloblastoma reverse transcriptase was obtained from Seikagaiku, St. Petersburg, Fla.; RNase H, DNA polymerase I, T4 DNA polymerase, and all restriction enzymes were from Bethesda Research Laboratories, Bethesda, Md.;

S1 nuclease was from Boehringer Mannheim, West Germany; RNase Block and T3 RNA polymerase were obtained from Stratagene, La. Jolla, Calif.; T7 RNA polymerase (80 units/μl) was obtained from Promega, Madison, Wis.; and radioactive nucleotide triphosphates were from Amersham, Arlington Heights, Ill. Oligonucleotides were synthesized on a BioSearch Model 8600 synthesizer and were purified by acrylamide gel electrophoresis prior to use. The rat β-actin clone in the pCD vector was isolated by hybridization to the published sequence (Nudel et al., Nuc. Acids Res. 11: 1756–1771 (1983)). pGEM-2 plasmids containing alpha subunit sequences of $G_s$, $G_o$, $G_{i1}$, $G_{i2}$, $G_{i3}$ were prepared according to Jones et al., J. Biol. Chem. 262: 1421–14249 (1987). IB15 cDNA (cyclophilin) cloned into the pCD vector was prepared according to Sutcliffe et al., Cold Spring Harbor Symposia on Quantitative Biology 48: 477–484 (1983).

cDNA synthesis

Total RNA was extracted from whole rat cerebellum by guanidium thiocyanate extraction followed by cesium chloride gradient ultracentrifugation (Chirgwin et al., Biochemistry 24: 5294–5299 (1987)). 40 μg of total RNA was primed with 100 ng of primer (5' AAA CGA CGG CCA GTG AAT TGT AAT ACG ACT CAC TAT AGG CGC (T)$_{15}$ 3') as schematized in FIG. 1. The RNA/primer mix was subjected to three cycles of heat denaturation at 80° C. alternating with incubation on ice for 3 minutes each. First strand synthesis was performed with avian myeloblastoma virus reverse transcriptase, and second strand cDNA was synthesized using RNase H and E. coli DNA polymerase I (Gubler et al., Gene 25: 263–269 (1983)). cDNA was made blunt ended by treatment with 2 units T4 DNA polymerase for 15 minutes at 37° C. Unincorporated triphosphates were removed by drop dialysis against double-distilled $H_2O$ for 2 hours, using a 0.025 mm nitrocellulose filter (Millipore, Bedford, Mass.). Identical reactions were performed for each synthesis with and without incorporation of 30 uCI of 400 Ci/mM α-$^{32}$P dCTP.

aRNA synthesis 3 ng of cDNA was amplified in each reaction. Reactions conditions were: 40 mM Tris pH 7.5, 6 mM $MgCl_2$, 10 mM NaCl, 2 mM spermidine, 10 mM DTT, 500 μM each ATP, GTP, and UTP, 12.5 μM CTP, 30 uCI α-$^{32}$P-CTP (3000 Ci/mM). 10 units RNase Block, and 80 units T7 RNA polymermerase in a volume of 20 μl. Reactions were carried out for 2 hours at 37° C. Incorporated radioactivity was determined by TCA precipitation and scintillation counting of Cerenkov radiation (Maniatis et al., supra)

In Situ Transcription (IST) and amplifications

Fresh frozen cerebellar tissue was cut by cryostat in a horizontal plane into 11 μm thick sections and processed for in situ transcription (IST) as previously described (Tecott et al., Science 240: 1661–1664 (1988)). oligonucleotide hybridization proceeded for 12 hours followed by washing for 5 hours in 0.5×SSC at room temperature. The IST reaction conditions were the same as described in Eberwine et al., Neuroscience Short Course I (Society for Neuroscience) 69–81 (1988), with the autoradiographic signals generated using a ration of 250 nM $^{32}$P dCTP/2.5 uM dCTP in the reaction. The cDNA used in amplifications was synthesized by IST using 250 uM each of DATP, dGTP, TTP and dCTP. After the IST, cDNA transcripts were isolated (Tecott et al., Science 240: 1661–1664 (1988)), and second strand cDNA was synthesized as described (Maniatis et al., supra). The hairpin-loop structure was removed by S1-nuclease treatment for 5 minutes. Subsequently the cDNA was blunt-ended using T4 DNA polymerase. After phenol/chloroform extraction and ethanol precipitation with 5 micrograms of carrier tRNA, cDNA was dissolved in 10 microliters of $H_2O$ and drop dialyzed for 4 hours against $H_2O$. The cDNA was removed and 2 uL was used for each aRNA amplification. Amplifications were performed as previously described with the exception that the concentration of nonlabeled CTP in the reaction was 1.25 uM rather than 12.5 uM.

Single cell injections and amplifications

Primary cultures of cerebellar neurons were established from rat embryos at gestation day 20, using techniques described in Gruol et al., J. Neurosci. 7: 1271–1293 (1987). Cultures consisting of Purkinje neurons, cerebellar interneurons, and glia were grown on polylysine in modified Eagles medium with 10% added serum. Identified mature Purkinje cells at 21 days in vitro were selected for cDNA synthesis. The whole-cell patch clamp recording technique (Yool et al., J. Neurosci. 8: 1971–1980 (1988)) was used to introduce the components for first strand synthesis intracellularly, while continuously monitoring cell physiology. Polished, uncoated patch electrodes (3–5 MOhm) were filled with 8–10 μl of the reaction mix, consisting of buffered saline (154 mM KCl, 6 mM NaCl, 5 mM $MgCl_2$, 0.1 μM $CaCl_2$, 10 mM Hepes pH 7.3), reverse transcriptase (2 units/μl), T7$_{55}$ oligonucleotide primer (0.5 ng/μl), and 1 mM each of dATP, dCTP, dGTP, TTP. The duration of loading and incubation in the whole-cell recording configuration ranged from 5–20 min. Simultaneous monitoring of electrical properties of the cell (sustained spontaneous firing, resting membrane potential near −60 mV, and input resistance >100 MOhm) indicated the loading process did not impair functions that are sensitive to damage.

The soma of each cell was harvested after loading with suction applied through the electrode holder after opening the electrode tip by gently touching it against the culture plate. Separate electrodes were used for each cell. Harvested soma were incubated individually in the electrodes for 1 hr at 37° C. to facilitate first strand synthesis, then ejected from the electrodes into EDTA (10 mM) in two volumes of ethanol, and frozen on dry ice. The samples were processed by addition of 5 μg of tRNA and NaCl to a final concentration of 500 mM and centrifuged to precipitate the nucleic acids. Residual cellular protein was removed by phenol/chloroform extraction and the nucleic acid concentrated and further purified by two ethanol precipitations. The nucleic acid was dissolved in 25 μl of $H_2O$ and heated at 95° C. for 3 minutes followed by quick cooling on ice to separate the cDNA from RNA. To make second-strand cDNA, the volume was increased to 50 μl with 2× concentrated DNA polymerase buffer (Maniatis et al., supra) and incubated with 10 units of DNA polymerase at 37° C. for 60 minutes. This mixture was phenol/chloroform extracted followed by two ethanol precipitations. The DNA was treated with 1 unit of S1 nuclease for 5 minutes (Maniatis et al., supra) to remove the hairpin-loop structure and the sample was phenol/chloroform extracted and ethanol precipitated. The ends of the DNA were blunt-ended by incubation of the DNA with 5 units of T4 DNA polymerase and 200 μM each of the deoxynucleotide triphosphates (Maniatis et al., supra) at 37° C. for 15 minutes followed by phenol/chloroform extraction and ether extraction. This DNA mixture was drop dialyzed against 50 ml of $H_2O$ for 4 hours. The DNA was then concentrated to 10 μl under vacuum. Between 3 and 5 μl of this material was used in each amplification reaction. aRNA amplification was done essentially as described above with the exception that nonlabeled dCTP was used at a final concentration of 1.25 μM and, when using 3 μl of DNA template, the amount of $^{32}$P-labeled dCTP was increased to 50 uCi.

Northern and Southern analyses

Swiss-Webster mouse and Sprague-Dawley rat genomic DNA were isolated as described (Maniatis et al. supra). 20 µg of each species DNA was digested overnight with 20 units of the following enzymes: BamHI, EcoRI, PstI. The DNA was electrophoresed on a 1% agarose gel and blotted to nitrocellulose (Maniatis et al., supra). pCD-actin was restriction enzyme digested with 10 units PvuII. $G_s$, $G_o$, $G_{i1}$, $G_{i2}$, and $G_{i3}$ containing plasmids were digested with restriction enzymes as follows: $G_s$: EcoRI and BamHI; $G_o$: EcoRI and EcoRV; $G_{i1}$: EcoRI and XbaI; $G_{i2}$: EcoRI and Sau96; and $G_{i3}$: EcoRI and EcoRV. These restriction enzyme digestions yield DNA fragments that have been used as specific probes for individual G protein alpha subunits (Jones et al., J. Biol. Chem. 262: 14241–14249 (1987)). pCD-IB15 was digested with BamHI (Sutcliffe et al., supra). Restriction digested plasmids (10 µG each for all G-protein plasmids and actin, and 5 ug for IB15) were electrophoresed on a 1% agarose gel and transferred to nitrocellulose as for the genomic DNA. Northern blots of whole mouse brain and rat cerebellar RNA (15 µG each) were made by blotting 1.2% agarose/3% formaldehyde gels to nitrocellulose in 20× SSC buffer (Maniatis et al., supra). Size standards (1.4 kb and 0.7 kb) for Northern blots were provided by the in vitro transcription of linearized positive control pGEM-2 plasmid with T7 RNA polymerase. Southern and Northern transfers were pre-hybridized overnight at 42° C. in: 50% formamide, 6× SSC, 5× Denhardt's solution, and 100 µg/µl sheared, autoclaved salmon sperm DNA. For hybridization, $2.5 \times 10^6$ cpm of aRNA was added to the bag and incubated in the same buffer for 48 hours at 42° C. Blots were washed in 0.1× SSC/0.2% SDS for 1 hour at 42° C. and exposed to Kodak XAR film at −80° C. with a Cronex intensifying screen (DuPont, Wilmington, Del.) for suitable time periods.

General characteristics of aRNA amplification

For the general characteristics of aRNA amplification, see, Melton et al., Nuc. Acids Res. 12: 7035–7056 (1984), which is incorporated herein by reference, which utilized in vitro transcription from plasmid vectors using SP6 RNA polymerase. The degree of amplification obtained was strongly dependent on the enzyme concentration and incubation time. Using the same amount of template (3 ng) and varying the amount of T7 RNA polymerase from 10 units to 80 units provided a 4-fold improvement in yield of aRNA. Maximum levels of amplification were obtained from incubation times between 2 and 4 hours; for incubations longer than 4 hours, TCA precipitable radioactivity began to decrease. In optimizing the reaction, it was found that increased UTP concentration (to 1 mM) during amplification increases aRNA synthesis, while inclusion of glycogen (used as a nonspecific carrier during cDNA precipitation) inhibits the aRNA reaction. Additionally, excess primer acts as an inhibitor of the reaction.

In order to assess the role of additional sequence located 5' to the T7 promoter site in aRNA production (potentially necessary to stabilize the enzyme-DNA interaction), amplifications were performed with synthetic primer lengths of 38, 57, and 80 nt, identical except for additional 5' sequence derived from Bluescript plasmid. Although cDNA generated from all three primers amplified equally well, the 57 nt primer (termed $T7_{57}$) gave the best yield of cDNA and was used for all subsequent amplification reactions. Additionally, cDNA primed with a T3 RNA polymerase promoter site (55 nucleotides long containing a 3' poly dT tract of 15 bases) was amplified with T3 RNA polymerase. This promoter-polymerase combination also generates a similar size distribution of amplified material, but yields approximately 75% of TCA-precipitable radioactivity as compared to equal units of T7 RNA polymerase. Using cDNA synthesized from total cerebellar RNA with the $T7_{57}$ primer, an 80-fold molar amplification was achieved as measured by TCA-precipitable radioactivity.

Amplification of a broad range of mRNA sequences from total cerebellar RNA

Because the 5' promoter sequence is specific for T7 RNA polymerase (Chamberlin et al., J. Biol. Chem. 248: 2235–2244 (1973) and Chamberlin et al., in *The Enzymes*, ed. P. Boyer (Academic Press, New York) pp. 87–108 (1982)) and the RNA polymerase is capable of producing transcripts of 7 kb or larger (Melton et al., supra), it was expected that the aRNA, produced would represent accurately the size and complexity of the synthesized cDNA. To test this, cDNA was synthesized from total cerebellar RNA using the $T7_{57}$ primer. A nonlabeled portion of this cDNA was then amplified with T7 RNA polymerase in the presence of $\alpha$-$^{32}$P CTP. The size distribution of cDNA and aRNA were very similar.

To characterize further the aRNA produced, Southern blot analysis of mouse and rat genomic DNA were performed using labeled aRNA derived from rat cerebellum as a probe. The aRNA hybridized to a broad distribution of sequences, indicating considerable sequence heterogeneity in the amplified material. Additionally, the aRNA showed marked sequence specificity for rat genomic DNA over that of mouse. A similar experiment was performed using aRNA to probe a Northern blot of whole rat cerebellar RNA. Again, the aRNA bound to a wide range of sequences indicating sequence heterogeneity in the amplified material. Approximately 30% of the total grain density of the bound material was found in the 18S and 28S ribosome bands. This is consistent with the yield of cDNA corresponding to these RNA species when cDNA is made from total RNA, suggesting that aRNA abundance is representative of the parent cDNA.

In order to quantify the complexity of amplified material, $R_o t$ hybridization analysis (Van Ness et al., Nuc. Acids Res. 10: 8061–8077 (1982)) of the aRNA was performed. Although a variety of hybridization and RNase conditions were tested, it was not possible to adequately reduce the non-hybridized background of the aRNA; 40% of total single-stranded aRNA remained TCA-precipitable after 500 µg/ml RNase A treatment in 0.5M NaCl at 37° C. for 30 minutes. This material was fully digested following sample boiling. Thus, the heterogeneous amplified material has considerable secondary and tertiary structure.

Detection of specific sequences in aRNA synthesized from nanogram quantities of cDNA In order to be useful in the detection and characterization of regulated transcripts, an amplification method must be able to amplify low-abundance transcripts. To detect such transcripts, aRNA was generated from 3 ng of cerebellar cDNA which had been primed with the $T7_{57}$ primer. The aRNA was labeled to a specific activity of $5 \times 10^8$ cpm/µg. $2.5 \times 10^6$ cpm were used to probe 10 µg each of plasmids containing inserts for rat actin, and the alpha subunits of rat G-proteins $G_s$, $G_o$, $G_{i1}$, $G_{i2}$ and $G_{i3}$. The vector sequences in each lane serve as an internal non-specific hybridization control. Following washing of filters in 0.1×SSC/0.1% SDS at 42° C., strong signals were visible in the actin and $G_s$ lanes. Other G protein mRNAs were not visible using this exposure time; however, since the $G_i$ and $G_o$-protein alpha subunits share considerable homology, this may be due to dilution of the aRNA for these G-protein alpha subunits among the multiple DNA restriction fragments encoding these sequences. In order to test this possibility, the presence of particular messages in the aRNA was assayed by probing slot-blots of aRNA and parent cDNA with random hexamer-primed probes for actin and the (G-proteins. Qualitatively identical results were found for both cDNA and aRNA: a very strong signal was discerned for the actin probe in both aRNA and cDNA, a weaker signal was observed for $G_s$, and very weak signals were discerned for $G_o$, $G_{i1}$, and $G_{i3}$.

Detection of specific aRNA transcripts from cerebellar tissue sections

The determined IST autoradiographic signal suggested that cDNA synthesis occurred in many cell types, with high signal density in the granule cell layer of the cerebellum. This result reflects the expected increase in amount of A+-mRNA in regions of high cellular density. In parallel experiments, this signal was comparable to the cDNA signal generated using oligo-dT (36 bases long) as a primer and is at least an order of magnitude greater than the signal generated from background non-specific IST signals produced from endogenous primer-template complexes. The aRNA produced from IST-generated cDNA contains sequences for IB15 (band at approximately 680 nucleotides) and actin was also determined. The variations in hybridization intensities reflect differences in the abundance of aRNAs encoding each of these molecules, as well as the differing amounts of radioactivity incorporated into aRNA for longer mRNAs versus shorter mRNAs. Background is minimal as shown by the lack of hybridization of aRNA to the pCD vector in the IB15 sample and the lack of binding to the DNA ladder. The actin and $G_s$ signals on the autoradiogram correspond to DNAs of 3 kilobases in length and longer, because the cDNAs encoding these proteins were not separated from the plasmid vector by restriction enzyme digestion and hence appear in multimer forms of the supercoiled plasmid.

Characterization of amplification products from a single cell

A schematic of the microinjection technique used to introduce the $T7_{57}$-oligonucleotide into individual Purkinje cells was prepared. The cerebellar primary culture provides access to identified Purkinje cells throughout their development to maturity by three weeks in vitro. The mature stage of an individual Purkinje cell is characterized by extensive dendritic outgrowth, expression of Purkinje-cell specific immunohistochemical markers, and endogenous pacemaker firing activity properties (Gruol et al., supra) comparable to Purkinje neurons of similar age in vivo.

The amount of radiolabel incorporated into aRNA obtained from single cell amplifications from individual Purkinje cells ranged from 30,000 to 300,000 cpm. The reasons for this variability are unclear, but may result from different amounts of first strand cDNA synthesis, variable success in regeneration of functional T7 RNA polymerase promoter site during the preparation of the cDNA template or partial degradation of the $T7_{57}$-oligonucleotide (Wickstrom, J. Biochem. Biophys. Methods 13: 97–102 (1986)). This low number of radioactive counts precluded the use of single cell aRNA as a probe to screen for specific low abundance mRNAs, yet was sufficient to serve as a probe for cerebellar RNA to gauge the complexity of the amplified material. The aRNA probe hybridized to poly(A)+ and total RNA isolated from the rat cerebellum. The specificity of this RNA signal is evident in the lack of hybridization of aRNA to E. coli total RNA and pBluescript DNA.

In addition to amplifying an entire population of $A^+$-mRNA using a single primer complex, degenerate primers have been utilized to amplify specific sequences for a specific class of mRNAs. In attempts to clone receptors that are part of the G-protein coupled receptor family, a T7-amplification oligonucleotide primer which uses a sequence common to all of these receptors was synthesized as the primer (rather than oligo-dT$_{15}$ which will prime a majority of mRNAs). The primer was used to prime cDNA synthesis from mRNA isolated from NG108-15 cells. This first strand cDNA was then processed as described above. The population of resultant aRNA molecules was less "complex" than that made using the T7-57 primer and contains sequences for the receptors of interest. As is the case for hybridization of specific probes to mRNA in Northern analyses, the generation of aRNAs specific to certain mRNAs is only limited by the specificity of the sequences used to prime cDNA synthesis. For degenerate primers, reference is made to Gould et al., Proc. Natl. Acad. Sci. U.S.A. 86: 1934–1938 (1989), which is incorporated herein by reference.

From the foregoing, it will be appreciated that novel techniques have been devised for the in vitro amplification of heterogeneous, complex populations of cDNA by generating cDNA with a primer containing a phage RNA polymerase promoter sequence. The technique is capable of greater than 80 to 1000 or more-fold molar amplification of starting cDNA. Amplified, anti-sense RNA (aRNA) produced by these techniques can be prepared that closely matches the size distribution of the parent cDNA. The amplified material contains heterogeneous sequences as determined by binding of aRNA to genomic Southern blots and specific Northern blots; additionally, detection of specific messages of various abundances in the amplified material can be performed.

Moreover, the spectrum of aRNA produced during amplification qualitatively reflects the population of cDNA from which it is produced. Since relative amounts of individual sequences present in cDNA represent (to a first approximation) their relative abundances in the transcribed RNA population and since aRNA production appears to be linear, the amount of a specific RNA in an aRNA population should reflect its abundance in the original RNA population. Given this, results from both aRNA-probed Southern blots and slot-blots of aRNA and cDNA probed with actin and G-protein cDNAs suggest that actin mRNA is considerably more abundant in rat cerebellum than any of the G-alpha mRNAs tested. Of greater interest is the finding that $G_s$-alpha produced a substantially higher hybridization signal than signals from the other G-alpha sequences tested. This is surprising because $G_s$-alpha protein levels are lower than those of other G-alpha subunits in a variety of tissues (Gilman, Ann. Rev. Biochem. 56: 615–649 (1987)), including brain (Gierschik et al., Proc. Natl. Acad. Sci. U.S.A. 83: 2258–2262 (1986)). Such high relative abundance of $G_s$-alpha mRNA has, however, been detected in other brain regions by in situ hybridization (Largent et al., Proc. Natl. Acad. Sci. U.S.A. 85: 2864–2868 (1988)) as well as in the NG108 neuronal cell line. These results are consistent with the hypothesis that unique control of regulation for $G_s$-alpha in rates of protein turnover and/or mRNA translation may exist (Largent et al., supra).

Although the foregoing invention has been described in some detail by way of illustration and example for purposes of clarity of understanding, it will be apparent that certain changes and modifications may be practiced within the scope of the appended claims.

We claim:

1. A gene expression library derived from a cell or tissue sample, comprising two or more specific nucleic acid messages of various abundances, whose levels of representation relative to other messages within a population reflect the physiologic state of the sample, thereby permitting diagnosis of a disease or condition, wherein said library is prepared by the following steps:

(a) adding a primer complex to a population of messenger RNAs (mRNAs) from said cell or cell population, said primer complex comprising:
  (i) a primer sequence complementary to a plurality of said population of mRNAs of said cell or cell population, and
  (ii) a promoter sequence in antisense orientation, wherein said primer complex hybridizes to said plurality population of mRNAs;
(b) synthesizing double-stranded complementary deoxyribonucleic acid (cDNA) by
  (i) extending said primer complex to form a first cDNA strand, and
  (ii) synthesizing a second cDNA strand complementary to said first cDNA strand without using an exogenous primer, wherein said second cDNA strand comprises said promoter sequence in sense orientation;
(c) linearly transcribing multiple copies of double-stranded cDNA into antisense RNAs (aRNAs) initiated from the promoter region of the primer complex; and
(d) quantitating specific aRNAs corresponding to specific mRNAs, wherein a plurality of said aRNAs represents an expression spectrum in said cell or cell population.

2. The gene expression library of claim 1 wherein the relative levels of pathogen-specific sequences allow a determination of infection.

3. The gene expression library of claim 1 wherein two or more specific nucleic acid messages are detected by hybridization.

4. The gene expression of claim 3 wherein hybridization is by northern or Southern blot.

5. An expression library of a cell or cell population, prepared by the following steps:

(a) adding a primer complex to a population of messenger RNAs (mRNAs) from said cell or cell population, said primer complex comprising:
  (i) a primer sequence complementary to a plurality of said population of mRNAs of said cell or cell population, and
  (ii) a promoter sequence in antisense orientation, wherein said primer complex hybridizes to said plurality of said population of mRNAs;
(b) synthesizing double-stranded complementary deoxyribonucleic acid (cDNA) by
  (i) extending said primer complex to form a first cDNA strand, and
  (ii) synthesizing a second cDNA strand complementary to said first cDNA strand without using an exogenous primer, wherein said second cDNA strand comprises said promoter sequence in sense orientation;
(c) linearly transcribing multiple copies of double-stranded cDNA into antisense RNAs (aRNAs) initiated from the promoter region of the primer complex; and
(d) quantitating specific aRNAs corresponding to specific mRNAs, wherein a plurality of said aRNAs represents an expression library in said cell or cell population.

6. The expression library of claim 5 wherein the sample is brain, spleen, bone, heart, vascular lung, kidney, liver, pituitary, endocrine glands, lymph node, dispersed primary cells, or tumor cells.

7. The expression library of claim 5 wherein the sample is blood and the expression of the hemoglobin is reduced relative to other messages and is diagnostic of thalassemia.

8. The expression library of claim 5 wherein said population comprises two or more RNAs.

9. The expression library claim 5, wherein said primer sequence consists essentially of polythymidylate (poly(dT)).

10. The expression library of claim 5, wherein said promoter is a bacteriophage promoter.

11. The expression library of claim 10, wherein said promoter is a T3, T7, or SP6 promoter.

12. The expression library of claim 11, further comprising the expression spectrum of a different cell or cell population or, alternatively, within the same cell or cell population in a different physiologic state wherein a difference in spectrum is indicative of an abnormal physiologic state.

13. The expression library of claim 5, wherein said aRNAs are quantitated by hybridization to nucleic acid sequences complementary to said aRNAs.

14. The expression library of claim 13, wherein said nucleic acid sequences are detected by the presence of a label or by Southern hybridization.

15. A method of determining the presence of thalassemia disease, comprising the steps of:

(a) adding primer complexes to a population of mRNAs from a mammalian cell or cell population, each primer complex comprising:
  (i) a primer sequence complementary to a plurality of said mRNAs of said cell or cell population, and
  (ii) a promoter sequence in antisense orientation, wherein said primer complexes hybridize to said plurality of said mRNAs;
(b) synthesizing double-stranded complementary deoxyribonucleic acid (cDNA) by
  (i) extending said primer complex to form a first cDNA strand, and
  (ii) synthesizing a second cDNA strand complementary to said first cDNA strand without using an exogenous primer, wherein said second cDNA strand comprises said promoter sequence in sense orientation;
(c) linearly transcribing multiple copies of double-stranded cDNA into antisense RNAs (aRNAs) initiated from the promoter region of the primer complexes; and
(d) quantitating specific aRNAs corresponding to specific mRNAs;

wherein quantitation of said aRNAs generates an expression spectrum reflecting the population of mRNAs in said cell or cell population, allowing for the identification of abnormal hemoglobin gene expression, thus permitting determination of a thalassemia disease.

16. The method of claim 15, wherein said mammalian cell or cell population is from blood.

17. The method of claim 15, wherein said mammalian cell or cell population is a human cell or cell population.

18. The method of claim 15, comprising the additional step of comparing said expression spectrum with a normal expression spectrum of a healthy cell or cell population, wherein abnormal levels of hemoglobin gene expression is indicative of a thalassemia disease.

19. The method of claim 15, wherein said promoter is a bacteriophage promoter.

20. The method of claim 19, wherein said promoter is a T3, T7, or SP6 promoter.

21. The method of claim 15, wherein said aRNAs are quantitated by hybridization to a nucleic acid sequence complementary to said aRNAs.

22. The method of claim 21, wherein said aRNAs are detected by the presence of a label.

23. The method of claim 21, wherein said aRNAs are detected by Southern hybridization.

24. A kit for detecting a thalassemia disease comprising a plurality of primer complex species and instructions for use of said primer complex species in a suitable container means, wherein said primer complex species comprise at least one primer sequence complementary to a plurality of hemoglobin genes and a promoter sequence in antisense orientation.

25. The kit according to claim 24, further comprising:
  (a) a reverse transcriptase;
  (b) an RNA polymerase;
  (c) dATP, dCTP, dGTP, and dTTP nucleotides; or
  (d) rATP, rCTP, rGTP, and UTP nucleotides.

26. A method of detecting the expression of mutant hemoglobin genes in a mammalian cell or cell population, comprising the steps:
  (a) adding primer complexes to a population of mRNAs from said mammalian cell or cell population, each primer complex comprising
    (i) a primer sequence complementary to a plurality of said mRNAs of said cell or cell population, and
    (ii) a promoter sequence in antisense orientation,
  wherein said primer complexes hybridize to said plurality of said mRNAs;
  (b) synthesizing double-stranded complementary deoxyribonucleic acid (cDNA) by
    (i) extending said primer complex to form a first cDNA strand, and
    (ii) synthesizing a second cDNA strand complementary to said first cDNA strand without using an exogenous primer, wherein said second cDNA strand comprises said promoter sequence in sense orientation;
  (c) linearly transcribing multiple copies of double-stranded cDNA into antisense RNAs (aRNAs) initiated from the promoter region of said primer complexes; and
  (d) quantitating specific aRNAs corresponding to specific mRNAs;
wherein the quantitation of said aRNAs indicates expression of mutant hemoglobin genes in said cell or cell population, as compared to expression of hemoglobin genes in a normal mammalian cell or cell population.

27. A method of identifying a pathogen-specific nucleic acid sequence in a cell or tissue of a mammal, comprising the steps:
  (a) adding a primer complex to a population of nucleic acid sequences from said cell or tissue, said primer complex comprising
    (i) a primer sequence complementary to a plurality of pathogen-specific nucleic acid sequences, and
    (ii) a promoter sequence in antisense orientation,
  wherein said primer complex hybridizes to said plurality of pathogen-specific nucleic acid sequences;
  (b) synthesizing double-stranded complementary deoxyribonucleic acid (cDNA) by
    (i) extending said primer complex to form a first cDNA strand, and
    (ii) synthesizing a second cDNA strand complementary to said first cDNA strand without using an exogenous primer, wherein said second cDNA strand comprises said promoter sequence in sense orientation; and
  (c) linearly transcribing multiple copies of double-stranded cDNA into antisense RNAs (aRNAs) initiated from the promoter region of said primer complex;
wherein the presence of said aRNAs is indicative of at least one pathogen-specific nucleic acid sequence in said cell or tissue.

28. The method of claim 27, wherein said mammal is a human.

29. The method of claim 27, wherein said cell or tissue is obtained from blood, brain, spleen, bone, heart, vascular tissue, lung, kidney, liver, pituitary, endocrine glands, lymph node, dispersed primary cells and tumor cells.

30. The method of claim 27, wherein said pathogen-specific nucleic acid sequence is a DNA sequence.

31. The method of claim 27, wherein said pathogen-specific nucleic acid sequence is a RNA sequence.

32. The method of claim 27, wherein said promoter is a bacteriophage promoter.

33. The method of claim 32, wherein said promoter is a T3, T7, or SP6 promoter.

34. The method of claim 27, wherein said aRNAs are quantitated by hybridization to pathogen-specific nucleic acid sequences.

35. The method of claim 34, wherein said nucleic acid sequences are detected by the presence of a label.

36. The method of claim 34, wherein said nucleic acid sequences are detected by Southern hybridization.

37. A method of identifying at least one member of a gene family in a cell or tissue, comprising the steps of:
  (a) adding a primer complex to a population of mRNAs from said cell or tissue, said primer complex comprising:
    (i) a primer sequence complementary to mRNAs of said gene family, and
    (ii) a promoter sequence in antisense orientation,
  wherein said primer complex hybridizes to a commonly shared sequence in said mRNAs of said gene family;
  (b) synthesizing double-stranded complementary deoxyribonucleic acid (cDNA) by
    (i) extending said primer complex to form a first cDNA strand, and
    (ii) synthesizing a second cDNA strand complementary to said first cDNA strand without using an exogenous primer, wherein said second cDNA strand comprises said promoter sequence in sense orientation; and
  (c) linearly transcribing multiple copies of double-stranded cDNA into antisense RNAs (aRNAs) initiated from the promoter region of said primer complex;
wherein the presence of said aRNAs is indicative of at least one member of a gene family in said cell or tissue.

38. The method of claim 37, wherein said promoter is a bacteriophage promoter.

39. The method of claim 38, wherein said promoter is a T3, T7, or SP6 promoter.

40. The method of claim 37, wherein said aRNAs are quantitated by hybridization to a nucleic acid sequence complementary to said aRNAs.

41. The method of claim 40, wherein said nucleic acid sequence is detected by the presence of a label.

42. The method of claim 40, wherein said nucleic acid sequence is detected by Southern hybridization.

43. A method of identifying alternatively spliced mRNA transcripts of a gene in a cell or tissue, comprising the steps of:
  (a) adding a primer complex to a population of mRNAs from a cell or tissue, said primer complex comprising
    (i) a primer sequence complementary to said gene, and
    (ii) a promoter sequence in antisense orientation,
  wherein said primer complex hybridizes to said MRNA transcripts of said gene;

(b) synthesizing double-stranded complementary-deoxyribonucleic acid (cDNA) by
  (i) extending said primer complex to form a first cDNA strand, and
  (ii) synthesizing a second cDNA strand complementary to said first cDNA strand without using an exogenous primer, wherein said second cDNA strand comprises said promoter sequence in sense orientation; and
(c) linearly transcribing multiple copies of double-stranded cDNA into antisense RNAs (aRNAs) initiated from the promoter region of said primer complex;
wherein the presence of aRNAs of variant lengths reflects alternatively spliced mRNA transcripts of said gene in said cell or tissue.

44. The method of claim 43, wherein said promoter is a bacteriophage promoter.

45. The method of claim 43, wherein said promoter is a T3, T7, or SP6 promoter.

46. The method of claim 43, wherein said aRNAs are quantitated by hybridization to a nucleic acid sequence complementary to said aRNAs.

47. The method of claim 46, wherein said nucleic acid sequence is detected by the presence of a label.

48. The method of claim 46, wherein said nucleic acid sequences are detected by Southern hybridization.

49. A method for identifying genetic polymorphisms of a gene in a cell or cell population, comprising the steps of:
(a) adding a primer complex to a population of mRNAs from a cell or cell population, the primer complex comprising:
  (i) a primer sequence complementary to a plurality of mRNAs from said gene, and
  (ii) a promoter sequence in antisense orientation,
wherein the primer complex hybridizes to said plurality of mRNAs;
(b) synthesizing double-stranded complementary deoxyribonucleic acid (cDNA) by
  (i) extending the primer complex to form a first cDNA strand, and
  (ii) synthesizing a second cDNA strand complementary to the first cDNA strand without using an exogenous primer, wherein the second cDNA strand comprises said promoter sequence in sense orientation;
(c) linearly transcribing multiple copies of double-stranded cDNA into antisense RNA (aRNA) initiated from the promoter region of the primer complex; and
(d) determining the sequence of the aRNAs;
wherein differences in the aRNA sequences are indicative of genetic polymorphisms in said cell or cell population.

50. The method of claim 49, wherein said promoter is a bacteriophage promoter.

51. The method of claim 49, wherein said promoter is a T3, T7, or SP6 promoter.

52. The method of claim 49, wherein said aRNAs are separated by hybridization to a nucleic acid sequence complementary to said aRNAs prior to sequence determination.

53. The method of claim 52, wherein said nucleic acid sequences are detected by Southern hybridization.

54. The method of claim 52, wherein said nucleic acid sequences are detected by the presence of a label.

* * * * *

UNITED STATES PATENT AND TRADEMARK OFFICE
CERTIFICATE OF CORRECTION

PATENT NO.    :   5,891,636
DATED         :   April 6, 1999
INVENTOR(S)   :   Van Gelder et al.

It is certified that error appears in the above-identified patent and that said Letters Patent is hereby corrected as shown below:

Claim 1, column 17, line 28, delete "spectrum" and replace with "library".

Claim 6, column 17, line 64, insert a comma after "vascular".

Claim 9, column 18, line 6, insert "of" after "library".

Claim 43, column 20, line 66, delete "MRNA" and replace with "mRNA".

Claim 43, column 21, line 1, delete the hyphen after "complementary".

Signed and Sealed this

Twenty-eighth Day of September, 1999

*Attest:*

Q. TODD DICKINSON

*Attesting Officer*     *Acting Commissioner of Patents and Trademarks*